United States Patent [19]

Jones et al.

[11] Patent Number: 4,652,572
[45] Date of Patent: Mar. 24, 1987

[54] 2-(FURANYL ALKYLAMINO OR THIENYL ALKYLAMINO OR PHENYLALKYLAMINO)-3-CARBOXY (OR HYDROXY)-PYRIDINES

[75] Inventors: Martin Jones, Stevenage; Rodney C. Young, Bengeo, both of England

[73] Assignee: Smith Kline & French Laboratories Limited, Welwyn Garden City, England

[21] Appl. No.: 754,390

[22] Filed: Jul. 12, 1985

Related U.S. Application Data

[62] Division of Ser. No. 555,319, Nov. 25, 1983, Pat. No. 4,547,512, which is a division of Ser. No. 365,224, Apr. 5, 1982, Pat. No. 4,439,437.

[30] Foreign Application Priority Data

Apr. 28, 1981 [GB] United Kingdom ............... 8112986

[51] Int. Cl.$^4$ .................... C07D 409/12; A61K 31/44
[52] U.S. Cl. ..................................... 514/336; 514/340; 514/230; 514/228; 514/237; 514/318; 514/349; 514/352; 546/284; 546/283; 546/193; 546/281; 546/297; 546/316; 544/131; 544/124
[58] Field of Search ............... 546/284, 283, 193, 281, 546/297, 316; 544/131, 124; 514/336, 340, 230, 228, 237, 318, 349, 352

[56] References Cited

U.S. PATENT DOCUMENTS

| | | | |
|---|---|---|---|
| 3,932,644 | 1/1976 | Durant et al. | 514/341 |
| 3,954,782 | 5/1976 | Fleckenstein et al. | 546/306 |
| 4,218,452 | 8/1980 | Brown et al. | 514/272 |
| 4,234,588 | 11/1980 | Brown et al. | 514/272 |
| 4,238,493 | 12/1980 | Roantree et al. | 514/332 |
| 4,307,104 | 12/1981 | Roantree et al. | 514/212 |
| 4,469,696 | 9/1984 | Rosentreter et al. | 514/252 |

OTHER PUBLICATIONS

Derwent Abstract 38240C (WP 8000966) May 15, 1980.
Derwent Abstract 64650C (EP 15138) Sep. 3, 1980.

Primary Examiner—Jane T. Fan
Attorney, Agent, or Firm—Linda E. Hall; Stuart R. Suter; Alan D. Lourie

[57] ABSTRACT

This invention relates to 2-amino-3-hydroxy, and 3-carboxy pyridine derivatives, in which the amino group is substituted by a methylthioethyl, butyl or oxypropyl group bearing a terminal heterocyclic group. The compounds have histamine $H_2$-antagonist activity. A specific compound of this invention is 2-[2-(2-guanidino-4-thiazolylmethylthio)ethyl]amino pyridine 3-carboxylic acid.

6 Claims, No Drawings

2-(FURANYL ALKYLAMINO OR THIENYL ALKYLAMINO OR PHENYLALKYLAMINO)-3-CARBOXY (OR HYDROXY)-PYRIDINES

This is a division of application Ser. No. 555,319 filed Nov. 25, 1983, now U.S. Pat. No. 4,547,512 issued Oct. 15, 1985 which is a division of Ser. No. 365,224 filed Apr. 5, 1982 now U.S. Pat. No. 4,439,437 issued Mar. 27, 1984.

This invention relates to certain pyridine derivatives, processes for their preparation, pharmaceutical compositions containing them and their use as histamine $H_2$-antagonists.

Histamine, a physiologically active compound endogenous in mammals, exerts its action by interacting with certain sites called receptors. One type of receptor is known as a histamine $H_1$-receptor (Ash and Schild, Brit. J. Pharmac. Chemother. 27 427(1966)) and the actions of histamine mediated through these receptors are blocked by drugs commonly called "antihistamines" (histamine $H_1$-antagonists) a common example of which is mepyramine. A second type of histamine receptor is known as the $H_2$-receptor (Black et al. Nature 1972, 236, 385). These receptors are not blocked by mepyramine but are blocked by burimamide. Compounds which block these histamine $H_2$-receptors are called histamine $H_2$-antagonists.

Histamine $H_2$-antagonists are useful in treating disease conditions caused by the biological effects of histamine mediated through $H_2$-receptors, for example, as inhibitors of gastric acid secretion, in the treatment of inflammation mediated through histamine $H_2$-receptors and as agents which act on the cardiovascular system, for example, as inhibitors of effects of histamine on blood pressure mediated through histamine $H_2$-receptors.

Cimetidine is an example of a histamine $H_2$-antagonist. Cimetidine has been shown to be useful in the treatment of duodenal, gastric, recurrent and stomal ulceration, and reflux oesophagitis and in the management of patients who are at high risk from haemorrhage of the upper gastrointestinal tract.

According to the present invention there are provided compounds of the formula (I):

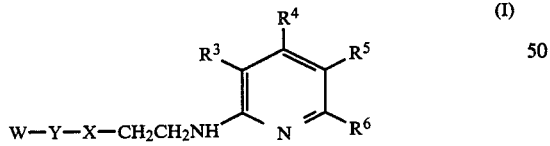

or a pharmaceutically acceptable salt thereof where

W is 4-imidazolyl optionally substituted in the 5-position with methyl or bromine; 2-pyridyl optionally substituted in the 3-position with $C_{1-4}$ alkyl, $C_{1-4}$ alkoxy, halogen, amino or hydroxy; 2-thiazolyl; 2-guanidino-4-thiazolyl; 2-furanyl or 2-thienyl optionally substituted in the 5-position with $R^1R^2N(CH_2)_m$- ; or phenyl substituted in the 3- or 4-position with a group $R^1R^2N(CH_2)_m$;

$R^1$ and $R^2$ which are the same or different are $C_{1-4}$ alkyl or together with the nitrogen atom represent piperidyl, pyrrolidyl or morpholinyl;

m is an integer from 1 to 4

X is methylene or sulphur

Y is methylene or, provided X is methylene and W is a substituted phenyl group, oxygen;

$R^3$ is carboxy or hydroxy;

$R^4$ is hydrogen or $C_{1-4}$ alkyl;

$R^5$ is hydrogen, $C_{1-4}$ alkyl, benzyl or with $R^4$ a $C_{3-5}$ alkylene group; and $R_6$ is hydrogen or $C_{1-4}$ alkyl.

W is preferably 5-methyl-4-imidazolyl or 2-guanidino-4-thiazolyl. Preferably X represents sulphur and Y represents methylene. $R^1$ and $R^2$ are preferably both methyl and m is preferably one.

In one group of compounds of the invention, $R^4$ and $R^6$ are both hydrogen. The invention also includes a group of compounds where $R^4$ or $R^5$ are methyl groups.

Particular compounds of the invention are 2-[2-(2-guanidino-4-thiazolylmethylthio)ethyl]aminopyridine 3-carboxylic acid and 2-[2-(5-methyl-4-imidazolylmethylthio)ethyl]amino-3-hydroxy-5-methylpyridine.

The compounds of the present invention are shown in formula (I) as being uncharged. However they can exist as Zwitterionic species by protonation of the nitrogen atom of the pyridine ring and the loss of a proton from the carboxy or hydroxy group $R^3$. The present invention includes such species. Also the compounds of formula (I) can form salts with bases as well as acid addition salts. Accordingly "pharmaceutically acceptable salts" means pharmaceutically acceptable salts with bases or pharmaceutically acceptable acid addition salts as the context requires. Examples of pharmaceutically acceptable salts with bases are alkali metal salts in particular the sodium salt.

Pharmaceutically acceptable acid addition salts of the compounds of formula (I) include those formed with hydrochloric, hydrobromic, sulphuric, phosphoric, acetic, citric, maleic, lactic, ascorbic and methanesulphonic acids.

The compounds of the present invention can be prepared by reacting an amine of the formula (II):

where W, Y and X are as defined for formula (I), with a pyridine derivative of formula (III):

where $R^4$, $R^5$ and $R^6$ are as defined for formula (I), Z is an atom or group displaceable by an amine, and $R^7$ is a carboxy group or a group convertible into a carboxy or a hydroxy group, and where $R^7$ in the product is a group convertible into a carboxy group or hydroxy group, converting $R^7$ into a carboxy or hydroxy group. Examples of groups convertible into carboxy are cyano, and carboxylic acid ester groups in particular $C_{1-4}$ alkoxycarbonyl groups. An example of a group convertible into hydroxy is benzyloxy. Z is preferably a halogen atom, e.g. chlorine, bromine or iodine.

The conversion of these groups into carboxy or hydroxy can be carried out by standard methods e.g. by hydrolysis.

Reaction of a compound of formula (II) with a compound of formula (III) can be conveniently effected by heating the compounds together, in particular by fusing them together, e.g. at a temperature of 110°–150° C. The reaction can also be effected in a solvent.

Salts of compounds of formula (I) can be formed by standard procedures for example by reacting with a base, for example an alkali metal hydroxide in a $C_{1-4}$ alkanol with an acid in a $C_{1-4}$ alkanol or by the use of an ion-exchange resin. Salts of compounds of formula (I) can be interconverted using an ion-exchange resin.

Compounds of formula (III) where $R^7$ is a cyano or $C_{1-4}$ alkoxycarbonyl group can be prepared by known methods (see H. Kurihara et al, J.Het.Chem 14, 1977, 1077–9 and J.J. Baldwin et al, J.Org.Chem 43, 1978, 2529–35). Compounds of formula (III) where $R^7$ is a benzyloxy group can be prepared by reacting an alkali metal salt of a compound of formula (III) where $R^7$ is a hydroxy group, obtainable by known methods (see Berichte 69, 1936, 2603), with a benzyl halide.

The activity of the compounds of formula (I) as histamine $H_2$-antagonists can be demonstrated by their ability to inhibit histamine-stimulated secretion of gastric acid from the lumen-perfused stomachs of rats anaesthetised with urethane, and to reverse histamineinduced inhibition of contractions of the isolated rat uterus. There are actions of histamine which, according to Ash and Schild, Brit. J. Pharmac. Chemother. 27 247 (1966), are not mediated by histamine $H_1$-receptors.

The histamine $H_2$-antagonist activity of the compounds can also be demonstrated by the inhibition of histamine-stimulated acid secretion in the Heidenhain Pouch Dog, the inhibition of histamine-induced tachycardia in the isolated guinea pig right atrium and the inhibition of histamine-induced vasodilatation in the anaesthetised cat.

Inhibition of histamine-stimulated secretion of gastric acid can be measured by using lumen-perfused stomachs of rats anaesthetised with urethane using a modification of the method of Ghosh and Schild, Brit. J. Pharmac. Chemother. 13 54 (1958) as described in U.S. patent application Ser. No. 302,941.

Compounds of formula (I) and their pharmaceutically acceptable acid addition salts can be administered orally, parenterally, topically or rectally. They will normally be administered as a pharmaceutical composition.

The invention also provides pharmaceutical compositions comprising a compound of formula (I) or a pharmaceutically acceptable acid addition salt thereof and pharmaceutically acceptable carrier.

The pharmaceutical compositions can also comprise an accepted drug in addition to a compound of formula (I), for example a histamine $H_1$-antagonist, e.g. mepyramine.

The pharmaceutical carrier employed can be a solid or liquid. Examples of solid carriers are lactose, maize starch, potato starch, or modified starches, dicalcium phosphate, terra alba, sucrose, celluloses, talc, gelatin, agar, pectin, acacia, magnesium stearate and stearic acid. Examples of liquid carriers are syrup, peanut oil, olive oil, alcohol, propylene glycol, polyethylene glycols and water.

For oral administration if a solid carrier is used, the composition can be prepared in the form of a tablet, capsule containing powder or pellets, troche or lozenge. The amount of solid carrier in a unit dosage form will generally be from about 25 mg to about 300 mg. If a liquid carrier is used, the composition can be in the form of a syrup, emulsion, multiple emulsion, sterile injectable liquid or an aqueous or non-aqueous solution or liquid suspension. Other additives such as preservatives, for example antioxidants or antibacterials, and/or flavouring or colouring agents can also be included. The sterile injectable liquids can be prepared in ampoules, multidose vials or unit dose disposable systems. For topical application the preparation can be in a semi-solid form, for example a cream, paste, ointment or gel, or in a liquid or aerosol form. The composition can also be a suppository formulation. The pharmaceutical compositions are prepared by conventional techniques involving procedures such as milling, mixing, granulating and compressing, spray drying, freeze drying or dissolving or dispersing the ingredients as appropriate to the desired preparation.

The active ingredient is present in the compositions in an effective amount to block histamine $H_2$-receptors involved in the condition being treated. Preferably an oral dosage unit for the inhibition of gastric acid secretion contains 15 to 250 mg of a compound of formula (I) or a pharmaceutically acceptable salt thereof (calculated as the free base).

The pharmaceutical compositions of the invention will normally be administered to man for the treatment of gastric and duodenal ulcers and other conditions caused or exacerbated by gastric acidity in the same general manner as that employed for known histamine $H_2$-antagonists, due allowance being made in terms of dose levels for the potency of the compound of the present invention relative to known histamine $H_2$-antagonist drugs. The daily dosage regimen for an adult patient is an oral dose of 15 to 1500 mg (preferably 20 to 250 mg) or an intravenous, subcutaneous or intramuscular dose of 1.5 to 150 mg (preferably 5 to 20 mg) of compound of formula (I) or pharmaceutically acceptable salt thereof calculated as the free base, the composition being administered 1 to 6 times per day.

The dosage regimen for conditions other than acid secretion which are mediated through histamine $H_2$-receptors will be chosen appropriate to the condition, the route of administration and the relative potency of the compounds.

This invention also provides a method of blocking histamine $H_2$-receptors which comprises administering to an animal an effective amount to block said receptors of a compound of formula (I) or a pharmaceutically acceptable salt thereof.

The pharmaceutical compositions of the invention will normally be administered to man for the treatment of gastric and duodenal ulcers and other conditions caused or exacerbated by gastric acidity in the same general manner as that employed for known histamine $H_2$-antagonists, due allowance being made in terms of dose levels for the potency of the compound of the present invention relative to known histamine $H_2$-antagonist drugs.

The following Examples are given by way of illustration. All temperatures are in degrees Centigrade. NMR data are recorded in delta ppm.

EXAMPLE 1

An intimate mixture of powdered 2-(5-methyl-4-imidazolylmethylthio)ethylamine (1.71 g; 0.010 moles) and 2-chloropyridine-3-carboxylic acid (1.73 g; 0.011 moles) was heated to 150° for 6 hours. The resulting cooled glass was dissolved in a little water and neutralised by slow addition of 2N sodium hydroxide solution. At pH6, solid precipitated out of solution. This was filtered off, and recrystallised from water to give 2-[2-

(5-methyl-4-imidazolylmethylthio)ethyl]amino pyridine 3-carboxylic acid as small, colourless crystals (1.04 g) which sublimed at 98°.

EXAMPLE 2

An intimate mixture of 2-(2-thiazolylmethylthio)-ethylamine [prepared from 6.73 g; 0.020 moles of the dihydrobromide salt and sodium ethoxide (from 0.92 g; 0.040 g.atom of sodium in ethanol)] and 2-chloropyridine 3-carboxylic acid (3.15 g; 0.020 moles) was heated to 150° for 3 hours. The resulting brown residue was cooled, dissolved in a little water, and basified to pH5 by dropwise addition of 2N sodium hydroxide solution, to precipitate an oil. The latter was separated and dried, and chromatographed on a column of silica-gel using chloroform/ethyl acetate, (1:1). The crude product was then recrystallised from isopropanol to give 2-[2-(2-thiazolylmethylthio)ethyl]amino pyridine 3-carboxylic acid as a cream-coloured solid (0.36g, m.p. 133°–4° (softening above 123°).

EXAMPLE 3

(a) A mixture of ethyl 2-chloro-4,6-dimethyl pyridine 3-carboxylate (2.48g; 0.012 moles) and 2-(5-methyl-4-imidazolyl-methylthio)ethylamine (4.11 g; 0.024 moles) was heated to 140° for 6 hours. The cooled reaction mixture was dissolved in ethanol, adsorbed onto silica-gel, and chromatographed on silica gel using chloroform/methanol (20:1) as eluant. The crude product, ethyl 2-[2-(5-methyl-4-imidazolyl-methylthio)ethyl]amino-4,6-dimethyl pyridine-3-carboxylate, 2.45 g, was used without further purification in the next step.

(b) Ethyl 2-[2-(5-methyl-4-imidazolylmethylthio)ethyl]-amino-4,6-dimethylpyridine-3-carboxylate (2.45 g, 0.0070 moles) was hydrolysed by refluxing with an excess of conc. hydrochloric acid (20 ml) for 20 hours. The reaction mixture was next evaporated to dryness, dissolved in a little water and basified to pH7.5 using 2N sodium hydroxide solution. After evaporating off water, the residue was dissolved in ethanol and adsorbed onto silica gel, followed by chromatography on silica gel using chloroform/methanol (10:1). The crude product was recrystallised from water to give 2-[2-(5-methyl-4-imidazolylmethylthio)ethyl]amino-4,6-dimethyl pyridine-3-carboxylic acid (0.20 g) which sublimes with decomposition above 110°. NMR data: Im-CH$_3$ at 2.10; 2XCH$_3$ at 2.24 and 2.36; CH$_2$CH$_2$S at 2.66; NCH$_2$CH$_2$ at 3.59; Im-CH$_2$S at 3.70; pyr. 5$\underline{H}$ at 6.32; Im. 2$\underline{H}$ at 7.50 (measured in DMSO-d$^6$)

EXAMPLE 4

An intimate mixture of 2-(2-guanidino-4-thiazolylmethylthio)ethylamine (2.31 g; 0.010 moles) and 2-chloropyridine-3-carboxylic acid (1.58 g; 0.010 moles) was heated to 140° for 3 hours. After cooling the mixture, it was dissolved in hot water and the solution was filtered hot. On leaving the filtrate to stand, a solid mass deposited. This was filtered off and recrystallised from water to give 2-[2-(2-guanidino-4-thiazolylmethylthio)ethyl]aminopyridine-3-carboxylic acid (0.60 g) as a beige-coloured solid m.p. 141°–5°.

EXAMPLE 5

(a) A solution of N-[1-(hept-1-enyl)]-piperidine (18.13 g; 0.10 moles) in dry tetrahydrofuran (50 ml) was added dropwise to a stirred solution of ethoxymethylene malononitrile (12.21 g; 0.10 moles) in dry tetrahydrofuran (125 ml) under an atmosphere of dry nitrogen, whilst cooling in a solid CO$_2$/ethanol bath, keeping the temperature to −30° to −20°. After the exotherm had subsided, the mixture was allowed to warm to room temperature and was stirred for 2 hours. The mixture was next evaporated to dryness, and chromatographed on silica gel, eluting the desired band with benzene. The crude red-brown oil so obtained was extracted several times with hot petroleum spirit (bp 60°-80°) and allowed to cool, yielding yellow needles of 2-[2-(1-piperidino-hept-1-enyl)]ethylene-1,1-dicarbonitrile, 5.35 g, m.p. 96°.

(b) 2-[2-(1-Piperidino-hept-1-enyl)]ethylene-1,1-dicarbonitrile (4.70g; 0.018 moles) was dissolved in glacial acetic acid (30 ml) and treated with a solution of HBr in acetic acid (50 ml of 45% v/v), and the mixture was then maintained at 55° for two hours. The mixture was next cooled and poured into water (about 750 ml), followed by neutralisation with sodium carbonate solution to about pH6, precipitating an oil. This was extracted with chloroform (3×750 ml) and the extracts were combined, washed with water, and then dried over anhydrous magnesium sulfate. After stripping the solution to a brown oil, it was chromatographed on silica-gel, eluting the desired band with benzene. The pale yellow oil so obtained, 2-bromo-3-cyano-5-n-pentylpyridine (4.87 g), was used for the next stage without further purification.

(c) A mixture of 2-bromo-3-cyano-5-n-pentyl pyridine (4.87 g; 0.019 moles) and 2-(5-methyl-4-imidazolylmethylthio)ethylamine (3.29 g; 0.019 moles) was heated to 120° for 9 hours. The resulting brown mass was chromatographed on a column of silica-gel, eluting the product with ethyl acetate. The resulting oil corresponding to 2-[2-(5-methyl-4-imidazolylmethylthio)ethyl]amino-3-cyano-5-n-pentyl pyridine (3.20 g) was used directly for the next stage.

(d) The 2-[2-(5-methyl-4-imidazolylmethylthio)ethyl]-amino-3-cyano-5-n-pentylpyridine obtained above (2.53 g; 0.0074 moles) was treated with conc. hydrochloric acid (20 ml) and heated to reflux for 36 hours. After stripping the mixture to dryness, the residue was dissolved in a little water and basified to about pH6 with sodium carbonate solution giving a precipitate. The mixture was azeotroped to dryness and chromatographed on silica-gel using chloroform/ethanol (20:1) to collect the desired band. The 2-[2-(5-methyl-4-imidazolylmethylthio)ethyl]amino-5-n-pentylpyridine-3-carboxylic acid hemihydrochloride obtained (1.25 g) could not be crystallised and it was a straw-coloured glass. NMR data (DMSO-d$^6$):-CH$_3$CH$_2$ at 0.88 ; (CH$_2$)$_3$ at 1.1–1.7; Im- CH$_3$ at 2.24; pyr-$\overline{CH_2}$ at 2.47; CH$_2$CH$_2$S at 2.70; NCH$_2$C$\overline{H}_2$ at 3.64; ImC$\overline{H}_2$S at 3.82; pyr-4$\underline{H}$ at 7.93; pyr-6$\underline{H}$ at 8.12 and Im-2$\underline{H}$ at 8.40.

EXAMPLE 6

(a) Piperidine (34.0 g 0.40 moles) was cooled in a solid CO$_2$/ethanol bath. It was treated with anhydrous potassium carbonate (12.0 g; 0.087 moles), followed by the dropwise addition, with constant stirring of freshly distilled 3-phenylpropionaldehyde (26.8 g; 0.20 moles), keeping the temperature below 5° . After the exotherm had subsided, the mixture was stirred for 15 minutes at room temperature, then carefully filtered, with slight dilution using piperidine. The resulting viscous oil was next distilled at reduced pressure to yield N-[1-(3-phenylprop-1-enyl)]piperidine (28.8 g, bp. 115°/0.5 mm) and it was used immediately in the next stage.

(b) A solution of N-[1-(3-phenylprop-1-enyl)]-piperidine (24.7 g; 0.123 moles) in dry tetrahydrofuran (60 ml) was added dropwise to a stirred solution of ethoxymethylene malononitrile (15.0 g; 0.123 moles) in dry tetrahydrofuran (150 ml) under a dry nitrogen atmosphere, at −30° to −20° with stirring and cooling with a solid $CO_2$/ethanol bath. After the addition, the mixture was allowed to warm to room temperature, and it was stirred at room temperature for 2 hours, followed by evaporation to dryness. The resulting orange-red oil was purified by column chromatography using silica gel, and eluting the desired component with toluene/chloroform (2:1). The crude product oil was treated with glacial acetic acid to bring about crystallisation, and the orange crystals were washed with further glacial acetic acid to give 2-[2-(1-piperidino-3-phenylprop-1-enyl)]ethylene-1,1-dicarbonitrile (3.11 g. m.p. 153°–4°).

(c) 2-[2-(1-Piperidino-3-phenylprop-1-enyl)]ethylene-1,1-dicarbonitrile (3.00 g; 0.011 moles) was suspended in glacial acetic acid (20 ml) and treated dropwise, with stirring at room temperature with a solution of HBr in acetic acid (30 ml of 45% v/v). The temperature of the mixture rose to 35°, and it was stirred for 30 minutes. The cooled mixture was poured into water (200 ml) and neutralised with sodium carbonate solution to pH6, yielding a pale yellow precipitate. The precipitate was extracted with chloroform (3×100 ml), washed with water, and dried over anhydrous magnesium sulphate. The resulting yellow solution was stripped to dryness under vacuum leaving 2-bromo-3-cyano-5-benzyl pyridine (3.0 g) as a yellow oil which slowly crystallised on standing.

(d) A mixture of 2-(5-methyl-4-imidazolylmethylthio)ethylamine (1.94 g; 0.011 moles) and 2-bromo-3-cyano-5-benzyl pyridine (3.0 g; 0.011 moles) was heated to 110° for 16 hours. The resulting thick mass was cooled, and purified on a column of silica gel using ethyl acetate to collect the desired band. The 2.1 g of pale yellow oil so obtained spontaneously crystallised after a few hours, and it was recrystallised from isopropanol to give 2-[2-(5-methyl-4-imidazolylmethylthio)ethyl]amino-3-cyano-5-benzyl pyridine as pale cream-coloured crystals, mp 105°–6°.

(e) 2-[2-(5-Methyl-4-imidazolylmethylthio)ethyl]amino-3-cyano-5-benzyl pyridine (1.60 g; 0.0044 moles) was treated with conc. hydrochloric acid (15 ml) and heated to reflux for 48 hours. The resulting solution was diluted with water and evaporated to dryness under vacuum. The residual brown oil was dissolved in a little water and the solution was treated with sodium carbonate solution to precipitate an oil at pH5.5. The whole mixture was azeotroped to dryness with ethanol, and the residue was purified by column chromatography, eluting the desired component with chloroform/ethanol (10:1) on silica-gel. The crude product was crystallised from isopropanol to give 2-[2-(5-methyl-4-imidazolylmethylthio)ethyl]amino-5-benzyl pyridine 3-carboxylic acid monohydrochloride as a pale cream-coloured solid (0.60 g, mp 161°–3°).

EXAMPLE 7

(a) 2-Chloro-3-hydroxypyridine (9.47 g; 0.073 moles) was added to a solution of sodium ethoxide in ethanol (from sodium, 1.67 g; 0.073 g. atom). Sufficient dimethyl sulphoxide was added to dissolve all of the solid, and ethanol was removed in vacuo . To the resulting solution was added benzyl chloride (9.3 g; 0.073 moles) with cooling and stirring, and the reaction mixture was left to stir under reflux for 6 hours. Unreacted benzyl chloride, and solvent, were evaporated off under vacuum on a boiling water bath, and the residue was treated with water to precipitate out an oil which was extracted with chloroform, washed with N sodium hydroxide solution and dried over anhydrous magnesium sulfate. After removing the solvent, 2-chloro-3-benzyloxypyridine was obtained as a solid (11.63 g, mp 36°–8°).

(b) 2-(5-Methyl-4-imidazolylmethylthio)ethylamine (18.13 g; 0.105 moles) and 2-chloro-3-benzyloxypyridine (11.63 g; 0.053 moles) were mixed and heated to 120° for 9 days. The resulting reaction mixture was purified by chromatography using silica-gel, and chloroform as eluant. The red oil obtained, corresponding to 2-[2-(5-methyl-4-imidazolylmethylthio)ethyl]amino-3-benzyloxypyridine (1.85 g), was used in the next step without further purification.

(c) 2-[2-(5-Methyl-4-imidazolylmethylthio)ethyl]amino3-benzyloxypyridine (1.3 g; 0.0036 moles) was treated with conc. hydrochloric acid (10 ml) and heated to 60° for 4 hours. The reaction mixture was stripped in vacuo to a green oil, dissolved in methanol, treated with ethyl acetate and left to stand for 2 days. The red crystals obtained were filtered off and recrystallised from methanol/ethyl acetate to give 2-[2-(5-methyl-4-imidazolylmethylthio)ethyl]amino-3-hydroxypyridine dihydrochloride as dark red crystals (0.17 g, mp 210°–212°).

EXAMPLE 8

(a) Ethyl cyanoacetate (113.1 g, 1.0 mole) and cyclopentanone (100.9 g, 1.2 mole) were condensed together in benzene (190 ml) for 4 hours using acetic acid (16 ml) and β-alanine (0.67 g) as catalyst, water being removed continuously using a Dean and Stark apparatus. The benzene solution was washed with sodium chloride solution and then with water. The solution was dried over sodium sulfate before filtering and evaporating to an oil which crystallised to a fawn solid in almost quantitative yield mp 52°–4°.

(b) Cyclopentylidine cyanoacetic ester (105.3 g, 0.588 moles) in dry ethanol (500 ml) was stirred as dimethyl formamide dimethyl acetal (70 g, 0.588 moles) was dripped in over 10 minutes. The mixture was then refluxed for 6 hours and evaporated to a red oil in vacuo. The oil was dissolved in acetic acid (200 ml), and a solution of HBr in acetic acid (45% w/v, 200 ml) was added over 15 minutes at 40° . After reacting at 55° for 45 minutes, the majority of the acid was removed by distillation in vacuo before water was added and the mixture was then neutralised to pH7 and extracted with chloroform. The chloroform extracts were dried ($Na_2SO_4$), and after filtration the solvent was removed in vacuo. The crude product was partly purified by chromatography on silica using chloroform-ligroin (60°–80°) as eluant. Recrystallisation was from ligroin (60°–80°) to give 37.9 g of a product (mp 65.5°–66.5°). Further product was obtained as a hydrochloride by the addition of ethanolic HCl to the concentrated mother liquor above (8.5 g. mp 160°–180° with decomposition). The total yield for this step was 28.4%.

(c) 2-Bromo-3-carbethoxy-4,5-propanopyridine (36.0 g, 0.133 moles) and 2-(5-methyl-4-imidazolyl)methylthioethylamine (45.6 g, 0.266 moles) were fused at 110° for 4 hours and then cooled. The mixture was shaken with hot water and chloroform. The chloroform layer was separated, dried with Na$_2$SO$_4$ and evaporated to an oil in vacuo. The oil was crystallised with Ligroin (60°–80° C.) and the crystals were washed with hot ligroin to give product (35.7 g, 74% yield). A small portion of this product was recrystallised from isopropanol to give a product melting at 153°–4° C.

(d) 2-[2-(5-Methyl-4-imidazolylmethylthio)ethylamino]-3-carbethoxy-4,5-propanopyridine (15.0 g, 41.7 m.mole) and concentrated hydrochloric acid (36% w/v, 250 ml) were refluxed for 21 hours. The solution was evaporated to dryness in vacuo, ethanol being added to assist in removal of the water. The residue was rinsed with methanol and isopropanol and dried to give 2-[2-(5-methyl-4-imidazolylmethylthio)ethylamino]4,5-propanopyridine 3-carboxylic acid dihydrochloride (6.47 g, 38% yield; m.p. 208.5°–209°).

EXAMPLE 9

(a) 2-Bromo-3-carbethoxy-4-methylpyridine (5g, 20.5 m.mole) was fused with (2-(5-methyl-4-imidazolylmethylthio)ethylamine (3.5 g, 20.5 m.moles) at 130° for 5 hours. The crude product was purified by chromatography on silica gel using ethanol-chloroform as eluant. Recrystallisation of the product was from isopropanol (1.95 g, 28% m.p. 121°–121.5°).

(b) The ester prepared above (2.36 g, 7 m.moles) was hydrolysed by refluxing for 24 hours with conc. hydrochloric acid (20 ml). The crude product was obtained in the form of the acid by removing ethanol, water and hydrogen chloride from the reaction mixture by distillation in vacuo, redissolving the product in water, adjusting the pH to 7 with sodium hydroxide solution and then stripping to a brown oil under vacuum. Purification was by chromatography on silica, using methanol-chloroform eluant and recrystallisation from methanol/isopropanol which gave [2-(5-methyl-4-imidazolylmethylthio)ethylamino]-4-methylpyridine 3-carboxylic acid. (Yield 0.73 g, 33%; m.p. 143° C. with decomposition. $^1$H NMR: (DMSO-d$^6$) 2.12(s) CH$_3$ (imidazole);2.39(s) CH$_3$ (pyridine);2.63(m) NCH$_2$CH$_2$S; 3.54(m) NCH$_2$S, 3.70(s) CH$_2$S;6.15 (broad) exchangeable H's;6.38(d) 5-pyridine H; 7.57(s) 2-imidazole H;7.90(d) 6-pyridine H.

EXAMPLE 10

(a) 3-Hydroxy-5-methylpyridine (20.57 g, 0.188 mole) and sodium carbonate (28.4 g, 0.268 mole) in water (380 ml) were stirred for 2 hours in a solution of potassium iodide (52.4 g, 0.316 mole) and iodine (52.4 g, 0.412 mole) in water (380 ml), at 10°. The brown solid produced was filtered off, suspended in water (500 ml) and aqueous sodium hydroxide was added until a solution was formed. On bubbling sulfur dioxide into the solution for 1 hour at room temperature a solid precipitated which was removed by filtration. This product was shown by thin layer chromatography and nuclear magnetic resonance spectroscopy to be a mixture of 2-iodo-3-hydroxy-5-methylpyridine and 2,6-diiodo-3-hydroxy-5-methylpyridine. Separation was effected by chromatography on silica in a WATERS LC 500 HPLC system using ethyl acetate-dichloromethane as eluant to give the mono-iodinated product (11.8 g, mp 186°–7°) and the di-iodinated product (5.7 g, mp. 221°–3°). A further crop of pure mono-iodinated product was obtained from the sulfur dioxide-bubbled mother liquid, on standing for 1 week. (total yield −14.8 g, 33%).

(b) 2-Iodo-3-hydroxy-5-methylpyridine (13.5 g, 57.4 m.mole) was added to a solution of sodium ethoxide (57.4 m.mole, prepared freshly from sodium and dry ethanol (100 ml)). Dry dimethyl sulfoxide (250 ml) was added, and the ethanol was removed by distillation under reduced pressure. Benzyl chloride (7.27 g, 57.4 mole) was added portionwise with cooling and then the mixture was heated at 90°14 100° for 15 hours. The dimethyl sulfoxide was boiled off under reduced pressure, water was added (100 ml) and the product was extracted from this with chloroform. After drying with magnesium sulfate and evaporation under reduced pressure, a crude product was obtained (17.62 g, 94% yield) a tiny portion of which, after heating in water and then recrystallising from methanol-water, gave 2-iodo-3-benzyloxy-5-methylpyridine which was pure by N.M.R. (mp 83°–5°).

(c) Crude 2-iodo-3-benzyloxy-5-methylpyridine (24.3 g, 74.8 mmole) and 2-(5-methyl-4-imidazolyl)methylthio)ethylamine (25.6 g, 149.7 m.mole) were fused together for 4 days at 100°–110°. The crude product was isolated by chromatography on silica using ethanol-chloroform as eluant. Purification was effected by shaking a chloroform solution of the crude product with water adjusted to pH 10.5 with potassium carbonate, then drying with magnesium sulfate and evaporating under reduced pressure. (1.6 g of amorphous product, 5.8 %).

(d) 2-[2-(5-Methyl-4-imidazolyl-methylthio)ethylamino]-3-benzyloxy-5-methylpyridine (1.29 g, 3.5 mmole) was heated for 1 hour at 60° with conc. hydrochloric acid (excess). This mixture was then evaporated to dryness under reduced pressure and the residue was recrystallised from methanol and ethyl acetate to yield 2-[2-(5-methyl-4-imidazolylthio)ethylamino]-3-hydroxy-5-methylpyridine dihydrochloride (470 mg, 38% yield, mp 214°–216°).

EXAMPLE 11

Pharmaceutical Compositions

A pharmaceutical composition for oral administration is prepared containing

|   |   | % by weight |
|---|---|---|
| A | 2-[2-(2-guanidino-4-thiazolyl-methylthio)ethyl]amino pyridine 3-carboxylic acid | 55 |
|   | Dibasic calcium phosphate dihydrate | 20 |
|   | Approved coloring agent | 0.5 |
|   | Polyvinylpyrrolidone | 4.0 |
| B | Microcrystalline Cellulose | 8.0 |
|   | Maize Starch | 8.0 |
|   | Sodium glycollate | 4.0 |
|   | Magnesium Stearate | 0.5 | by mixing together the ingredients A (substituting lactose or microcrystalline cellose for dibasic calcium phosphate dihydrate if desired), adding a concentrated solution of polyvinylpyrrolidone and granulating, drying and screening the dried granules; adding the ingredients B to the dried granules and compressing the mixture into tablets containing 100 mg, 150 mg or 200 mg of the free base.

Other compounds of the invention, for example those specifically described in Examples 2 to 5 can be formulated into pharmaceutical compositions by a similar procedure.

A pharmaceutical composition for injectable administration is prepared by converting 2-[2-(2-guanidino-4thiazolylmethylthio)ethyl]amino pyridine 3-carboxylic acid into the tetrahydrochloride salt form and dissolving this in sterile water to give a 1 to 5% w/w solution. The solution is clarified by filtration and filled into vials which are sealed and sterilised. A suitable vial contains 2 ml of the solution.

What is claimed is:

1. A compound of the formula (I):

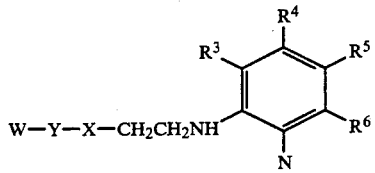

or a pharmaceutically acceptable salt thereof where:

W is 2-furanyl or 2-thienyl substituted or unsubstituted in the 5-position with $R^1R^2N(CH_2)_m$-or phenyl substituted in the 3- or 4-position with $R^1R^2N(CH_2)_m$;

$R^1$ and $R^2$ which are the same or different are $C_{1-4}$ alkyl or together with the nitrogen atom represent piperidyl, pyrrolidyl or morpholinyl, m is an integer from 1 to 4;

X is methylene or sulphur;

Y is methylene or, provided X is methylene and W is a substituted phenyl group, oxygen;

$R^3$ is carboxy or hydroxy;

$R^4$ is hydrogen or $C_{1-4}$ alkyl;

$R^5$ is hydrogen, $C_{1-4}$ alkyl, benzyl; and $R^6$ is hydrogen or $C_{1-4}$ alkyl.

2. A compound according to claim 1, where -Y-X- is methylthio.

3. A compound according to claim 1, where $R^4$ and $R^6$ are both hydrogen.

4. A compound according to claim 1, where $R^4$ or $R^5$ is methyl.

5. A pharmaceutical composition having histamine $H_2$-antagonist activity comprising an effective amount of a compound according to claim 1 and a pharmaceutically acceptable carrier.

6. A method of blocking histamine $H_2$-receptors which comprises administering to an animal in need of such treatment an effective amount to block said receptors of a compound according to claim 1.

* * * * *

UNITED STATES PATENT AND TRADEMARK OFFICE
CERTIFICATE OF CORRECTION

PATENT NO. : 4,652,572
DATED : March 24, 1987
INVENTOR(S) : Martin Jones and Rodney C. Young It is certified that error appears in the above-identified patent and that said Letters Patent is hereby corrected as shown below:

Claim 1, the structural formula should appear as follows:

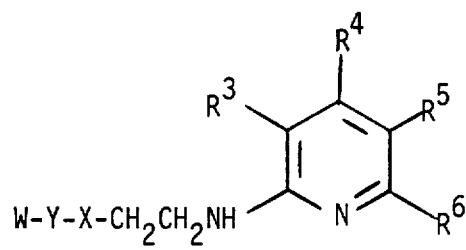

Signed and Sealed this

Twenty-ninth Day of December, 1987

*Attest:*

DONALD J. QUIGG

*Attesting Officer*   *Commissioner of Patents and Trademarks*